United States Patent [19]

Kinoshita et al.

[11] Patent Number: 5,523,464
[45] Date of Patent: Jun. 4, 1996

[54] BENZENESULFONAMIDE DERIVATIVES

[75] Inventors: Iwao Kinoshita; Haruki Takai; Nobuo Kosaka, all of Shizuoka; Katsura Sugawara, Machida; Akio Ishii; Hiroyuki Ishida, both of Shizuoka; Katsushige Gomi, Susono, all of Japan

[73] Assignee: Kyowa Hakko Kogyo Co., Ltd., Tokyo, Japan

[21] Appl. No.: 256,232

[22] PCT Filed: Nov. 5, 1992

[86] PCT No.: PCT/JP92/01429

§ 371 Date: Jan. 30, 1994

§ 102(e) Date: Jan. 30, 1994

[87] PCT Pub. No.: WO94/10135

PCT Pub. Date: Nov. 5, 1994

[51] Int. Cl.$^6$ .................. C07D 211/58; C07D 295/26; C07D 295/28; C07C 311/29
[52] U.S. Cl. .................. 560/140; 544/59; 544/161; 544/383; 546/159; 546/171; 546/223; 546/239; 546/240; 548/193; 548/194; 548/542; 564/88; 564/89; 562/833
[58] Field of Search .................. 544/59, 161, 383; 546/159, 171, 239, 223, 240; 548/193, 194, 542; 564/88, 89; 560/140

[56] References Cited

U.S. PATENT DOCUMENTS 4,879,315  11/1989  Magarian et al. .................. 514/754

FOREIGN PATENT DOCUMENTS 0395093  10/1990  European Pat. Off. .

OTHER PUBLICATIONS

J. Am. Chem. Soc., vol. 12, No. 22 (1990) pp. 7861–7868.

*Primary Examiner*—Emily Bernhardt
*Attorney, Agent, or Firm*—Fitzpatrick, Cella, Harper & Scinto

[57] ABSTRACT

The present invention relates to benzenesulfonamide derivatives represented by Formula (I):

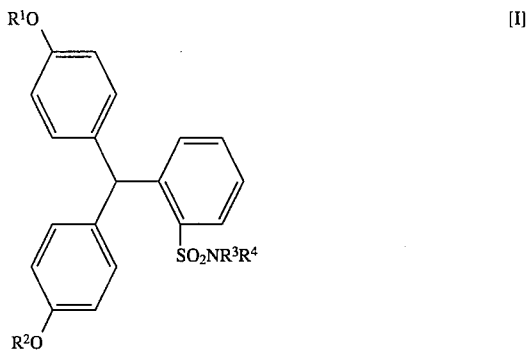

in which $R^1$ and $R^2$ independently represent hydrogen or lower alkanoyl; and $R^3$ and $R^4$ independently represent hydrogen, lower alkyl, cycloalkyl, substituted or unsubstituted polycycloalkyl, substituted aryl, or a substituted or unsubstituted heterocyclic group, or $R^3$ and $R^4$ are combined together with the adjacent nitrogen atom to form a substituted or unsubstituted aliphatic heterocyclic group, or a pharmaceutically acceptable salt thereof. The derivatives are useful as therapeutic agents for osteoporosis.

2 Claims, No Drawings

BENZENESULFONAMIDE DERIVATIVES

This application is a 371 of PCT/JP92/01429 filed Nov. 5, 1992.

TECHNICAL FIELD

The present invention relates to benzenesulfonamide derivatives which are useful as therapeutic agents for osteoporosis.

BACKGROUND ART

J. Amer. Chem. Soc., 112, 7861 (1990) discloses compounds represented by Formula (A)

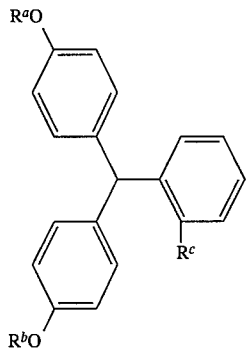
[A]

wherein $R^c$ represents sulfonanilide. Further, EP 395093 discloses that compounds represented by Formula (A) wherein $R^c$ represents carbamoyl etc. are useful as therapeutic agents for osteoporosis.

DISCLOSURE OF THE INVENTION

According to the present invention, there can be provided benzenesulfonamide derivatives represented by Formula (I):

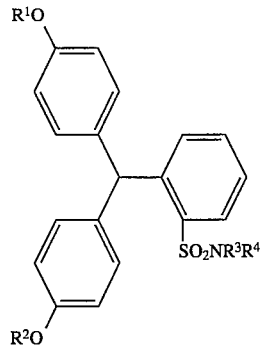
[I]

in which $R^1$ and $R^2$ independently represent hydrogen or lower alkanoyl; and $R^3$ and $R^4$ independently represent hydrogen, lower alkyl, cycloalkyl, substituted or unsubstituted polycycloalkyl, substituted aryl, or a substituted or unsubstituted heterocyclic group, or $R^3$ and $R^4$ are combined together with the adjacent nitrogen atom to form a substituted or unsubstituted aliphatic heterocyclic group [hereinafter referred to as Compound (I); the same applies to the compounds of other formula numbers], or pharmaceutically acceptable salts thereof.

In the definitions of the groups in Formula (I), the lower alkyl means a straight-chain or branched alkyl group having 1 to 8 carbon atoms such as methyl, ethyl, propyl, isopropyl, butyl, isobutyl, sec-butyl, tert-butyl, pentyl, neopentyl, hexyl, heptyl, and octyl. The lower alkanoyl means a straight-chain or branched alkanoyl group having 1 to 5 carbon atoms such as formyl, acetyl, propionyl, butyryl, isobutyryl, valeryl, and pivaloyl. The cycloalkyl means a cycloalkyl group having 3 to 8 carbon atoms such as cyclopropyl, cyclopentyl, cyclohexyl, cycloheptyl, and cyclooctyl. The polycycloalkyl means a saturated hydrocarbon group having (a) bridge(s) which is selected from the group consisting of compounds represented by the formula

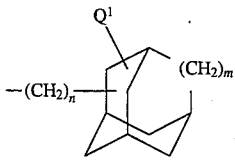

(in which $Q^1$ represents hydrogen or lower alkyl; m represents 0 or 1; and n represents an integer of 0 to 5) such as tricyclo[3.3.1.1$^{3,7}$]decyl and tricyclo[3.3.1.0$^{3,7}$]-nonyl, and compounds represented by the formula

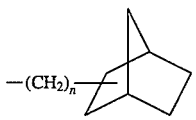

(in which n has the same meaning as defined above) such as bicyclo[2.2.1]heptyl. The lower alkyl in the definition of $Q^1$ has the same meaning as the above-defined lower alkyl.

The aryl means phenyl or naphthyl. The substituted aryl has 1 to 3 independently-selected substituents. The substituent includes, for example, lower alkyl, hydroxy, lower alkoxy, lower alkylthio, halogen, nitro, amino, lower alkanoyl, aroyl, carboxy, and lower alkoxycarbonyl. The alkyl moiety of the lower alkyl, the lower alkoxy, the lower alkylthio, and the lower alkoxycarbonyl has the same meaning as the above-defined lower alkyl. The lower alkanoyl and the aryl moiety of the aroyl have the same meanings as the above-defined lower alkanoyl and aryl, respectively. The halogen means fluorine, chlorine, bromine, and iodine atoms.

The heterocyclic group means an aromatic heterocyclic group such as pyridyl, quinolyl, and thiazolyl, or an aliphatic heterocyclic group such as pyrrolidinyl, piperidyl, piperidino, piperazinyl, morpholino, and thiomorpholino. The aliphatic heterocyclic group which is formed by combining $R^3$ and $R^4$ together with the adjacent nitrogen atom has the same meaning as the above-defined aliphatic heterocyclic group. The substituted heterocyclic group has 1 to 2 independently-selected substituents. The substituent includes, for example, lower alkyl, lower alkoxy, halogen, benzyl, and substituted or unsubstituted phenyl. The lower alkyl, the lower alkoxy, and the halogen have the same meanings as described above. The substituents of the substituted phenyl has the same meaning as the above-defined substituents for the aryl.

Examples of the pharmaceutically acceptable salts of Compounds (I) are acid addition salts with hydrochloric acid, hydrobromic acid, hydroiodic acid, nitric acid, phosphoric acid, formic acid, acetic acid, benzoic acid, maleic acid, fumaric acid, succinic acids, tartaric acid, citric acid, oxalic acid, glyoxylic acid, aspartic acid, methanesulfonic acid, ethanesulfonic acid, or benzenesulfonic acid.

The processes for producing Compounds (I) are described below.

Compound (I) can be prepared from the known Compound (II) which is obtained by a known method as described in J. Med. Chem., 31, 1978 (1988) according to the following reaction step(s):

Process

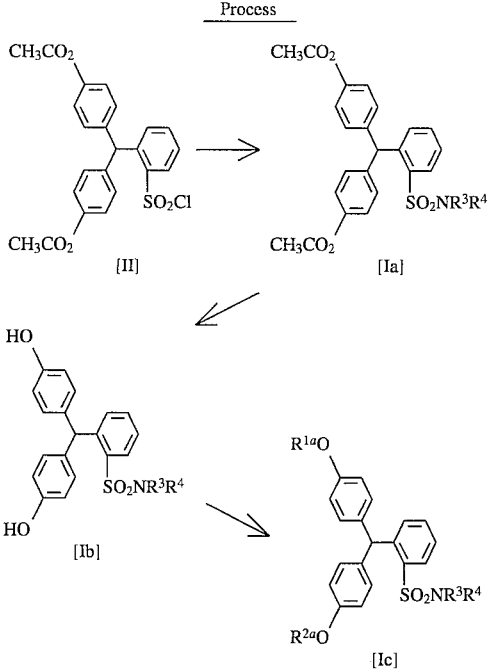

(wherein $R^{1a}$ and $R^{2a}$ mean groups other than hydrogen in the definitions of $R^1$ and $R^2$, respectively; and $R^3$ and $R^4$ have the same meanings as defined above.)

Compound (Ia) can be obtained by reacting Compound (II) with an amine (III) represented by the following formula $$HNR^3R^4 \qquad [III]$$

(in which $R^3$ and $R^4$ have the same meanings as defined above).

An amine (III) is used in an amount of 0.1 to 5 equivalents, preferably 0.5 to 2 equivalents, based on Compound (II). As the reaction solvent, any solvent can be used so long as the solvent is inert to the reaction. Halogenated hydrocarbons such as dichloromethane, chloroform, dichloroethane, and carbon tetrachloride, aromatic hydrocarbons such as benzene, toluene, and xylene, aromatic heterocyclic groups such as pyridine, ketones such as acetone and methyl ethyl ketone, alcohols such as methanol, ethanol, and isopropanol, ethers such as diethyl ether, dioxane, and tetrahydrofuran, amides such as formamide and dimethylformamide, acetonitrile, ethyl acetate, dimethylsulfoxide, water, or the like may be used as the reaction solvent either alone or in combination. Usually, the reaction is completed in 10 minutes to 48 hours at from 0° C. to the boiling point of the solvent used.

If desired, the reaction may be carried out in the presence of an inorganic base such as sodium hydroxide, potassium hydroxide, sodium carbonate, cesium carbonate, sodium bicarbonate, and silver oxide, or an organic base such as triethylamine, N,N-diisopropylethylamine, N-methylmorpholine, pyridine, and dimethylaminopyridine, so as to allow the reaction to proceed smoothly.

Compound (Ib), which is Compound (I) in which $R^1$ and $R^2$ are both hydrogen, can be obtained by hydrolysis of Compound (Ia) in the presence of a base. As the base, the inorganic bases as described above may be used. As the reaction solvent, water, or alcohols such as methanol, ethanol, and isopropanol may be used either alone or in combination. Usually, the reaction is completed in 30 minutes to 12 hours at from 0° C. to the boiling point of the solvent used.

Compound (Ic), which is Compound (I) in which $R^1$ and $R^2$ are alkanoyl, can be obtained by reaction of Compound (Ib) with an acylating agent. As the acylating agent, a reactive derivative of the corresponding carboxylic acid such as an acid anhydride and an acyl halide may be used. As the reaction solvent, those used in the reaction of Compound (II) and an amine (III) or the like may be used. Usually, the reaction is completed in 30 minutes to 24 hours at from 0° C. to the boiling point of the solvent used. If desired, the reaction may be carried out in the presence of the base as described above.

The intermediates and the desired compounds in the processes described above can be isolated and purified by purification methods conventionally used in organic synthetic chemistry, foe example, filtration, extraction, washing, drying, concentration, recrystallization, and various kinds of chromatography. If desired, the intermediates may be subjected to the subsequent reaction without purification.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable solvent, followed by addition of a suitable acid to form a salt.

Compounds (I) and pharmaceutically acceptable salts thereof may be in the form of adducts with water or various solvents, which are also within the scope of the present invention.

Typical examples of Compounds (I) are shown in Table 1.

TABLE 1

[Structure: diphenylmethane core with R¹O and R²O on two para-phenyl groups and SO₂NR³R⁴ on ortho position of third phenyl]

| Compd. No. | R¹ | R² | —NR³R⁴ |
|---|---|---|---|
| 1 | CH₃CO— | CH₃CO— | piperidin-1-yl |
| 2 | CH₃CO— | CH₃CO— | 2-adamantylamino (—NH-adamantyl) |
| 3 | CH₃CO— | CH₃CO— | 4-(2-chlorophenyl)piperazin-1-yl |
| 4 | CH₃CO— | CH₃CO— | (1-benzylpiperidin-4-yl)amino |
| 5 | CH₃CO— | CH₃CO— | isopropylamino |
| 6 | CH₃CO— | CH₃CO— | n-octylamino |
| 7 | CH₃CO— | CH₃CO— | 4-(2-methoxyphenyl)piperazin-1-yl |
| 8 | CH₃CO— | CH₃CO— | cycloheptylamino |
| 9 | CH₃CO— | CH₃CO— | cyclohexylamino |
| 10 | CH₃CO— | CH₃CO— | cyclooctylamino |

TABLE 1-continued
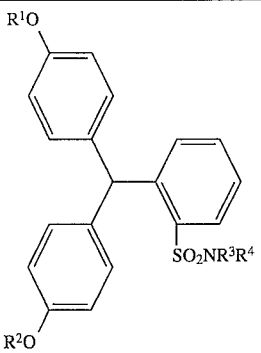
| Compd. No. | R¹ | R² | —NR³R⁴ |
|---|---|---|---|
| 11 | CH₃CO— | CH₃CO— | 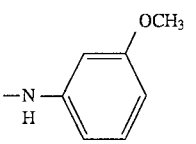 |
| 12 | CH₃CO— | CH₃CO— | 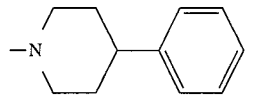 |
| 13 | H— | H— | 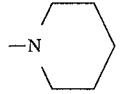 |
| 14 | H— | H— | 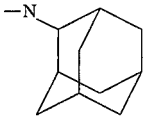 |
| 15 | H— | H— | 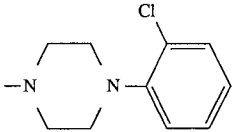 |
| 16 | H— | H— | 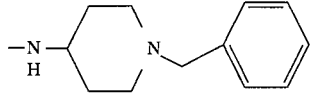 |
| 17 | H— | H— |  |
| 18 | H— | H— | 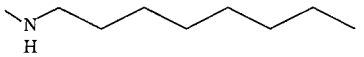 |
| 19 | H— | H— | 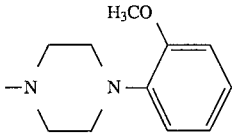 |
| 20 | H— | H— | 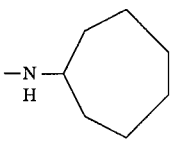 |

TABLE 1-continued
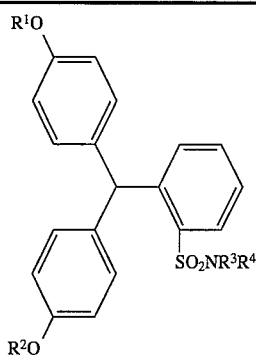
| Compd. No. | R¹ | R² | —NR³R⁴ |
|---|---|---|---|
| 21 | H— | H— | —NH-cyclohexyl |
| 22 | H— | H— | —NH-cyclooctyl |
| 23 | H— | H— | —NH-(3-methoxyphenyl) |
| 24 | H— | H— | —NH-sec-butyl |
| 25 | H— | H— | —NH-(4-phenylthiazol-2-yl) |
| 26 | H— | H— | —NH-(1-adamantyl) |
| 27 | H— | H— | —NH-(3-methylthiophenyl) |
| 28 | H— | H— | —NH-(2,4-dimethoxyphenyl) |

TABLE 1-continued

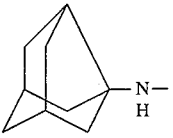

| Compd. No. | R¹ | R² | —NR³R⁴ |
|---|---|---|---|
| 29 | H— | H— | (adamantyl)-NH— |

The bone absorption-inhibiting effects of the compounds of the present invention are illustrated by test examples.

Test Example

Examination of Calcium Dissolution from Bone in vitro

A calvaria of a 5 to 6 day-old dd mouse was aseptically cut off, washed with Dulbecco's modified phosphate buffered saline not containing calcium and magnesium (manufactured by Gibco Oriental Co.) and separated along the sutura of its center. One half of the calvaria so separated was cultured in 1.5 ml of Dulbecco's modified Eagle medium (manufactured by Gibco Oriental Co.) containing thermally inactivated (at 56° C. for 20 minutes) horse serum (15%) and fetal calf serum (2.5%). The test compound was dissolved in dimethyl sulfoxide, and 10 μl ($1 \times 10^{-5}$M) of the solution so prepared was added to the culture. Parathyroid hormone (PTH) was dissolved in a 0.15M aqueous sodium chloride solution (pH 3), and 3 μl ($1 \times 10^{-8}$M) of the solution so prepared was added to the culture. The cultivation was carried out at 37° C. for 96 hours in an atmosphere of air (95%) and carbon dioxide (5%), and the culture medium was replaced with a fresh one after 48 hours from the beginning of the cultivation. Four groups consisting of a control group, a group treated with the test compound ($1 \times 10^{-5}$M), a group treated with PTH ($1 \times 10^{-8}$M), and a group treated with both the test compound and PTH were prepared in order to examine the effect of the test compound on dissolved calcium (i.e., absorption of bone) from the PTH-intensified bone. Absorption of bone was determined by measuring the quantity of calcium accumulated in the culture collected at the time of 96 hours of cultivation. The concentration of total calcium contained in the culture was measured with Calcium C-test Wako (manufactured by Wako Pure Chemicals Co., Ltd.), and the result of the test was represented by the inhibition rate calculated in accordance with the equation set forth below. Results obtained are shown in Table 2.

$$\text{Inhibition Rate (\%)} = (C_P - C_D)/(C_P - C_O) \times 100$$

$C_O$: Total calcium concentration in the culture containing neither PTH nor the test compound $C_P$: Total calcium concentration in the culture treated with PTH alone $C_D$: Total calcium concentration in the culture treated with both PTH and the test compound

TABLE 2

| Compd. No. | Rate of Inhibition of Bone-Absorption (10 μM; %) |
|---|---|
| 13 | 144 |
| 14 | 152 |
| 15 | 158 |
| 16 | 170 |
| 17 | 69 |
| 18 | 154 |
| 19 | 151 |
| 20 | 153 |
| 21 | 159 |
| 24 | 150 |
| 28 | 143 |

Compounds (I) and pharmaceutically acceptable salts thereof can be administered orally by being formulated into the form conventionally employed such as tablets, capsules, and syrups, or parenterally, for example as injections, as dropping preparations, or by rectal administration using suppositories. Such preparations administered orally or parenterally are produced by the conventionally known methods and may contain other ingredients such as excipients, lubricants, binders, disintegrators, isotonicities, and emulsifying agents. Examples of the pharmaceutically acceptable carrier used are water, distilled water for injection, saline, glucose, fructose, sucrose, mannitol, lactose, starch, cellulose, methyl cellulose, carboxymethyl cellulose, hydroxypropyl cellulose, alginic acid, talc, sodium citrate, calcium carbonate, calcium hydrogenphosphate, magnesium stearate, urea, silicon resins, sorbitan fatty acid esters, and glycerol fatty acid esters.

BEST MODE FOR CARRYING OUT THE INVENTION

EXAMPLE 1

1-{2-[Bis(4-acetoxyphenyl)methyl]benzenesulfonyl}-piperidine (Compound 1)

Piperidine (460 mg) and triethylamine (0.91 ml) was dissolved in dichloromethane (20 ml), and then 2-[bis(4-acetoxyphenyl)methyl]benzenesulfonyl chloride (3.12 g) obtained according to the method described in J. Med. Chem., 31, 1978 (1988) etc. was added thereto at room temperature. After stirring for 2 hours, water was added thereto. The organic layer was separated off, and the aqueous layer was extracted with chloroform. The chloroform layer was combined with the organic layer, and the combined organic layer was washed with a saturated aqueous sodium chloride solution and dried over anhydrous magnesium sulfate. The resulting solution was concentrated under reduced pressure to give 2.92 g of the desired Compound 1 as a solid.

NMR (CDCl$_3$) δ (ppm): 8.11, 7.68–6.99, 6.77, 3.02–2.90, 2.31, 1.40–1.28

In the following Examples 2 to 12, the desired compounds were obtained in a similar manner as in Example 1 except that corresponding amines were used in place of piperidine.

EXAMPLE 2

2-[Bis(4-acetoxyphenyl)methyl]-N-(tricyclo[3.3.1.1$^{3,7}$]decan-2-yl)benzenesulfonamide (Compound 2)

NMR (CDCl$_3$) δ (ppm): 8.14, 7.55–7.00, 6.95, 3.05, 2.34, 1.78–1.40

EXAMPLE 3

1-{2-[Bis(4-acetoxyphenyl)methyl]benzenesulfonyl}-4-(2-chlorophenyl)piperazine (Compound 3)

NMR (CDCl$_3$) δ (ppm): 8.15, 7.62–6.91, 6.78, 3.20–3.18, 2.80–2.61, 2.26

EXAMPLE 4

N-(1-Benzylpiperidin-4-yl)-2-[bis(4-acetoxyphenyl)methyl]benzenesulfonamide (Compound 4)

NMR (CDCl$_3$) δ (ppm): 8.12, 7.54–7.01, 6.84, 3.62–1.72, 2.80–2.61, 2.32

EXAMPLE 5

2-[Bis(4-acetoxyphenyl)methyl]-N-isopropylbenzenesulfonamide (Compound 5)

NMR (CDCl$_3$) δ (ppm): 8.05, 7.52–6.93, 6.82, 3.17, 2.29, 0.68

EXAMPLE 6

2-[Bis(4-acetoxyphenyl)methyl]-N-octylbenzenesulfonamide (Compound 6)

NMR (CDCl$_3$) δ (ppm): 8.07, 7.50–6.95, 6.81, 3.00, 2.29, 1.38–0.85

EXAMPLE 7

1-{2-[Bis(4-acetoxyphenyl)methyl]benzenesulfonyl}-4-(2-methoxyphenyl)piperazine (Compound 7)

NMR (CDCl$_3$) δ (ppm): 8.07, 7.60–6.80, 3.82, 3.28–3.15, 2.80–2.72, 2.30

EXAMPLE 8

2-[Bis(4-acetoxyphenyl)methyl]-N-cycloheptylbenzenesulfonamide (Compound 8)

NMR (CDCl$_3$) δ (ppm): 8.12, 7.60–7.00, 6.90, 2.31, 1.50–0.90

EXAMPLE 9

2-[Bis(4-acetoxyphenyl)methyl]-N-cyclohexylbenzenesulfonamide (Compound 9)

NMR (CDCl$_3$) δ (ppm): 8.08, 7.50–6.95, 6.83, 2.85, 2.28, 1.80–0.60

EXAMPLE 10

2-[Bis(4-acetoxyphenyl)methyl]-N-cyclooctylbenzenesulfonamide (Compound 10)

NMR (CDCl$_3$) δ (ppm): 8.10, 7.52–6.98, 6.89, 3.19, 1.60–1.20

EXAMPLE 11

2-[Bis(4-acetoxyphenyl)methyl]-N-(3-methoxyphenyl)benzenesulfonamide (Compound 11)

NMR (CDCl$_3$) δ (ppm): 8.10, 7.60–6.98, 6.75–6.05, 3.78, 2.40

EXAMPLE 12

1-{2-[Bis(4-acetoxyphenyl)methyl]benzenesulfonyl}-4-phenylpiperidine (Compound 12)

NMR (CDCl$_3$) δ (ppm): 8.25, 7.70–7.07, 6.85, 3.68–1.50, 2.35

EXAMPLE 13

1-{2-[Bis(4-hydroxyphenyl)methyl]benzenesulfonyl}piperidine (Compound 13)

In a mixture of 50 ml of a saturated aqueous sodium bicarbonate solution and 30 ml of ethanol was suspended 2.9 g of Compound 1 obtained in Example 1, followed by heating under reflux for 2 hours. The resulting mixture was concentrated under reduced pressure, and water was added to the residue. The resulting mixture was extracted with ethyl acetate, and the extract was dried over anhydrous magnesium sulfate. After concentration under reduced pressure, the residue was purified by silica gel chromatography to give 1.06 g of the desired Compound 13 as a solid.

Melting point: 109°–112° C.

IR (KBr) cm$^{-1}$: 3408, 1509, 1146

NMR (DMSO-d$_6$) δ (ppm): 9.22, 7.87–7.23, 6.83, 6.30, 2.90–2.80, 1.33–1.25

In the following Examples 14 to 23, the desired compounds were obtained in a similar manner as in Example 13 except that corresponding acetyl derivatives were used.

EXAMPLE 14

2-[Bis(4-hydroxyphenyl)methyl]-N-(tricyclo[3.3.1.1$^{3,7}$]decan- 2-yl)benzenesulfonamide (Compound 14)

Melting point: 99°–101° C.

IR (KBr) cm$^{-1}$: 3390, 1510, 1152

NMR (DMSO-d$_6$) δ (ppm): 9.28, 8.07, 7.68–7.31, 6.97, 6.71, 6.51, 3.08, 2.01–1.31

EXAMPLE 15

1-{2-[Bis(4-hydroxyphenyl)methyl]benzenesulfonyl}-4-(2-chlorophenyl)piperazine (Compound 15)

Melting point: 136°–139° C.

IR (KBr) cm$^{-1}$: 3420, 1511, 1151

NMR (DMSO-d$_6$) δ (ppm): 9.20, 8.00, 7.48–6.64, 6.42, 3.10–2.55

EXAMPLE 16

N-(1-Benzylpiperidin-4-yl)-2-[bis(4-hydroxyphenyl)methyl]benzenesulfonamide (Compound 16)

Melting point: 82°–85° C.

IR (KBr) cm$^{-1}$: 3325, 1508, 1160

NMR (DMSO-d$_6$) δ (ppm): 9.26, 7.92, 7.61–7.20, 6.89, 6.67, 6.40, 3.40–2.50, 1.90–1.20

EXAMPLE 17

2-[Bis(4-hydroxyphenyl)methyl]-N-isopropylbenzenesulfonamide (Compound 17)

Melting point: 89°–90° C.

IR (KBr) cm$^{-1}$: 3430, 1509, 1156

NMR (DMSO-d$_6$) δ (ppm): 9.30, 7.95, 7.65–7.21, 6.90, 6.67, 6.39, 3.20, 0.88

EXAMPLE 18

2-[Bis(4-hydroxyphenyl)methyl]-N-octylbenzenesulfonamide (Compound 18)

Melting point: 32°–34° C.

IR (KBr) cm$^{-1}$: 3410, 1510, 1154

NMR (DMSO-d$_6$) δ (ppm): 9.27, 7.88, 7.64–7.18, 6.85, 6.65, 6.36, 2.69–2.49, 1.32–0.78

EXAMPLE 19

1-{2-[Bis(4-hydroxyphenyl)methyl]benzenesulfonyl}-4-(2-methoxyphenyl)piperazine (Compound 19)

Melting point: 90°–92° C.

IR (KBr) cm$^{-1}$: 3400, 1511, 1145

NMR (DMSO-d$_6$) δ (ppm): 9.20, 7.93, 7.70–7.22, 6.84, 6.68, 3.72, 3.08–2.51

EXAMPLE 20

2-[Bis(4-hydroxyphenyl)methyl]-N-cycloheptylbenzenesulfonamide (Compound 20)

Melting point: 90°–94° C.

IR (KBr) cm$^{-1}$: 3294, 1512, 1161

NMR (DMSO-d$_6$) δ (ppm): 9.22, 7.91, 7.62–7.18, 6.85, 6.63, 6.38, 1.45–1.10

EXAMPLE 21

2-[Bis(4-hydroxyphenyl)methyl]-N-cyclohexylbenzenesulfonamide (Compound 21)

Melting point: 145°–150° C.

IR (KBr) cm$^{-1}$: 3375, 1507, 1151

NMR (DMSO-d$_6$) δ (ppm): 9.26, 7.93, 7.51–7.18, 6.88, 6.66, 6.39, 2.78, 1.60–0.80

EXAMPLE 22

2-[Bis(4-hydroxyphenyl)methyl]-N-cyclooctylbenzenesulfonamide (Compound 22)

Melting point: 87°–90° C.

IR (KBr) cm$^{-1}$: 3410, 1509, 1150

NMR (DMSO-d$_6$) δ (ppm): 9.22, 7.92, 7.60–7.20, 6.89, 6.67, 6.40, 3.10, 1.60–1.10

EXAMPLE 23

2-[Bis(4-hydroxyphenyl)methyl]-N-(3-methoxyphenyl)benzenesulfonamide (Compound 23)

Melting point: 75°–76° C.

IR (KBr) cm$^{-1}$: 3410, 1510, 1147

NMR (DMSO-d$_6$) δ (ppm): 9.29, 8.02, 7.59–6.51, 6.37, 3.69

EXAMPLE 24

2-[Bis(4-hydroxyphenyl)methyl]-N-(sec-butyl)benzenesulfonamide (Compound 24)

sec-Butylamine (430 mg) and triethylamine (2 ml) was dissolved in dichloromethane (20 ml), and then 2-[bis(4-acetoxyphenyl)methyl]benzenesulfonyl chloride (2.5 g) obtained according to the method described in J. Med. Chem., 31, 1978 (1988) etc. was added thereto at room temperature. After stirring for 80 minutes, water was added thereto. The organic layer was separated off, and the aqueous layer was extracted with chloroform. The chloroform layer was combined with the organic layer, and the combined organic layer was washed with a saturated aqueous sodium chloride solution and dried over anhydrous magnesium sulfate. The resulting solution was concentrated under reduced pressure. Then, 3.3 g of the residue obtained above was suspended in a mixture of 100 ml of a saturated aqueous sodium bicarbonate solution and 100 ml of ethanol, followed by heating under reflux for 6 hours. The resulting mixture was concentrated under reduced pressure, and water was added to the residue. The resulting mixture was extracted with ethyl acetate, and the extract was dried over anhydrous magnesium sulfate. After concentration under reduced pressure, the residue was purified by silica gel chromatography to give 1.67 g of the desired Compound 24 as a solid.

Melting point: 129°–130° C.

IR (KBr) cm$^{-1}$: 3335, 1512, 1155

NMR (DMSO-d$_6$) δ (ppm): 9.25, 7.92, 7.60–7.18, 6.85, 6.64, 6.38, 3.00, 1.42–0.60

In the following Examples 25 to 29, desired compounds were obtained in a similar manner as in Example 24 except that corresponding amines were used in place of secbutylamine.

EXAMPLE 25

2-[Bis(4-hydroxyphenyl)methyl]-N-(4-phenylthiazol-2-yl)benzenesulfonamide (Compound 25)

Melting point: 245°–300° C.

IR (KBr) cm$^{-1}$: 3424, 1509, 1170

NMR (DMSO-d$_6$) δ (ppm): 9.31, 8.00, 7.60–6.68, 6.39

EXAMPLE 26

2-[Bis(4-hydroxyphenyl)methyl]-N-(tricyclo[3.3.1.1$^{3,7}$]decan- 1-yl)benzenesulfonamide (Compound 26)

Melting point: 141°–144° C.

IR (KBr) cm$^{-1}$: 3400, 1512, 1149

NMR (DMSO-d$_6$) δ (ppm): 9.23, 8.00, 7.60–7.20, 6.88, 6.63, 6.39, 1.86–1.30

EXAMPLE 27

2-[Bis(4-hydroxyphenyl)methyl]-N-(3-methylthiophenyl)benzenesulfonamide (Compound 27)

Melting point: 80°–82° C.

IR (KBr) cm$^{-1}$: 3410, 1512, 1155

NMR (DMSO-d$_6$) δ (ppm): 9.21, 7.94, 7.60–7.00, 6.82–6.56, 6.32, 2.33

EXAMPLE 28

2-[Bis(4-hydroxyphenyl)methyl]-N-(2,4-dimethoxyphenyl)benzenesulfonamide (Compound 28)

Melting point: 109°–110° C.

IR (KBr) cm$^{-1}$: 3240, 1514, 1161

NMR (DMSO-d$_6$) δ (ppm): 9.40, 9.27, 7.77–6.32, 3.74, 3.46

EXAMPLE 29

2-[Bis(4-hydroxyphenyl)methyl]-N-(tricyclo[3.3.1.0$^{3,7}$]nonan- 3-yl)benzenesulfonamide (Compound 29)

Melting point: 175°–178° C.

IR (KBr) cm$^{-1}$: 3450, 1511, 1155

NMR (DMSO-d$_6$) δ (ppm): 9.20, 8.30, 7.97, 7.73, 7.55–7.21, 6.67, 2.20–1.30

Industrial Applicability

According to the present invention, there can be provided benzenesulfonamide derivatives which are useful as therapeutic agents for osteoporosis.

We claim:

1. A benzenesulfonamide compound represented by Formula (I):

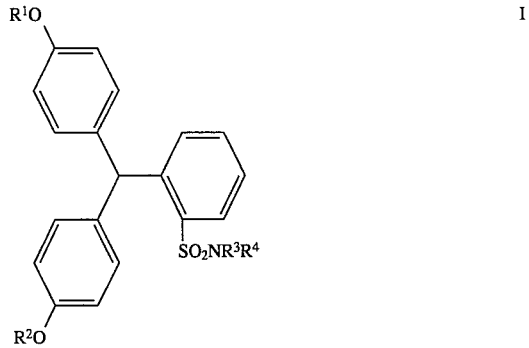

in which R$^1$ and R$^2$ independently represent hydrogen or lower alkanoyl; and R$^3$ and R$^4$ independently represent hydrogen or lower alkyl, or a pharmaceutically acceptable salt thereof.

2. 2-[Bis(4-hydroxyphenyl)methyl]-N-isopropylbenzenesulfonamide or a pharmaceutically acceptable salt thereof.

* * * * *